United States Patent [19]
Harlow et al.

[11] Patent Number: 5,987,160
[45] Date of Patent: Nov. 16, 1999

[54] METHOD AND APPARATUS FOR INSPECTING A PHOTORESIST MATERIAL BY INDUCING AND DETECTING FLUORESCENCE OF THE PHOTORESIST MATERIAL

[75] Inventors: Jeffrey Dean Harlow, Cicero; David A. Rockwell, Carmel, both of Ind.

[73] Assignees: Delco Electronics Corporation, Kokomo, Ind.; Hughes Electronics, Los Angeles, Calif.

[21] Appl. No.: 08/832,428

[22] Filed: Apr. 2, 1997

[51] Int. Cl.[6] ........................................................ G06K 9/00
[52] U.S. Cl. .............................................. 382/145; 348/131
[58] Field of Search ...................................... 382/141, 144, 382/145, 149; 430/8; 356/237.5; 348/87, 126, 131

[56] References Cited

U.S. PATENT DOCUMENTS

| | | | |
|---|---|---|---|
| 5,161,201 | 11/1992 | Kaga et al. | 382/141 |
| 5,265,170 | 11/1993 | Hine et al. | 382/8 |
| 5,576,948 | 11/1996 | Stern et al. | 382/145 |
| 5,598,345 | 1/1997 | Tokura | 382/145 |
| 5,607,800 | 3/1997 | Ziger | 382/145 |

*Primary Examiner*—Andrew W. Johns
*Attorney, Agent, or Firm*—Jimmy L. Funke

[57] ABSTRACT

A method and apparatus for inspecting a substrate having a surface on which a photoresist material has been deposited. The apparatus preferably includes a device for transporting substrates through an illumination beam such that the edges of the substrates are sequentially irradiated by the beam without requiring that each substrate be individually manipulated. The illumination beam is generated and projected onto the substrates by equipment configured to produce a beam having a size, wavelength, and intensity sufficient to cause the photoresist material to fluoresce with an intensity that can be detected without magnification. Inspection can be performed manually or automated through optical equipment that can detect flaws in the photoresist based on knowledge of the patterned image desired for the photoresist.

23 Claims, 1 Drawing Sheet

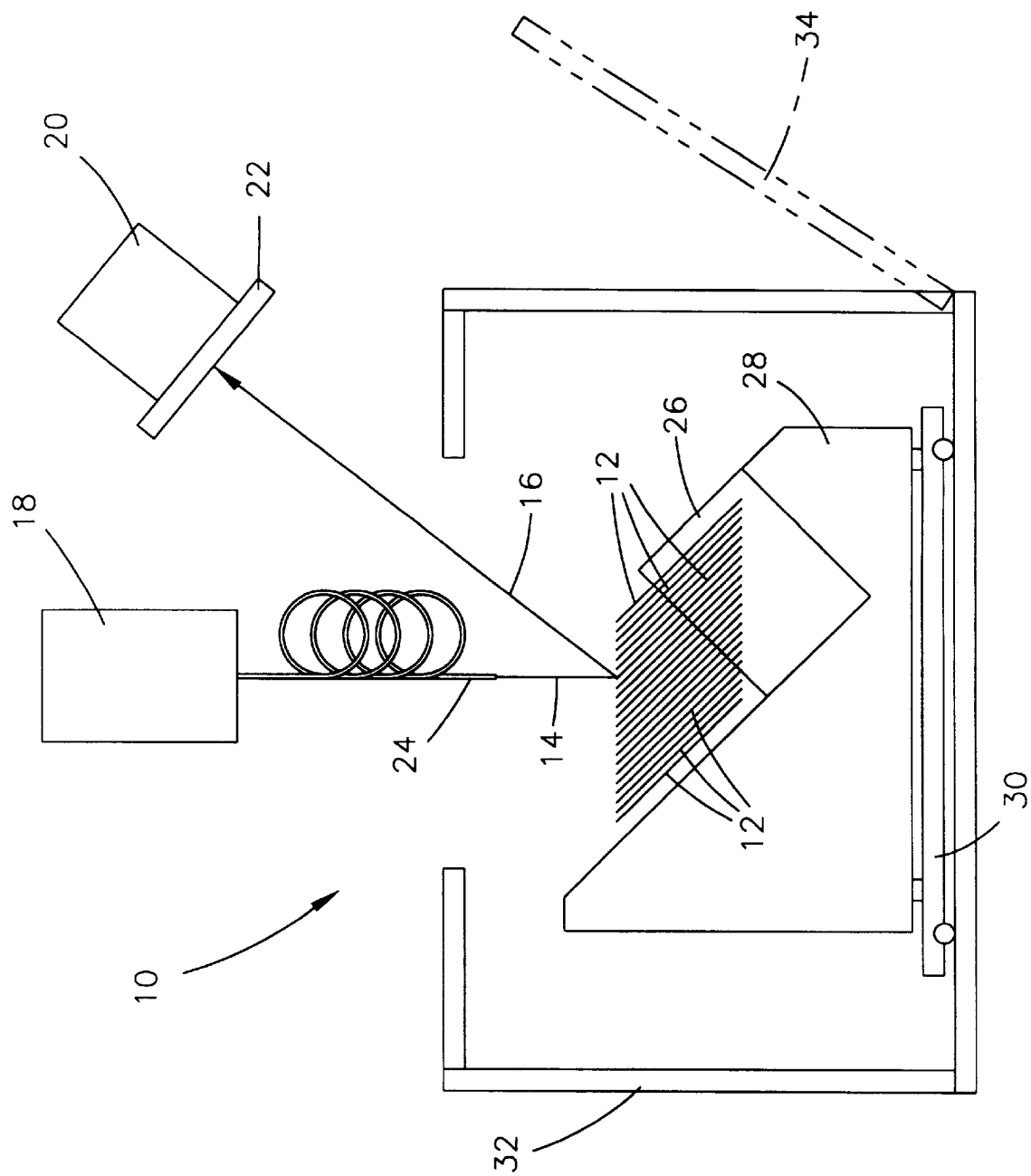

METHOD AND APPARATUS FOR INSPECTING A PHOTORESIST MATERIAL BY INDUCING AND DETECTING FLUORESCENCE OF THE PHOTORESIST MATERIAL

FIELD OF THE INVENTION

The present invention generally relates to processing techniques for semiconductor devices. More particularly, this invention relates to a method and apparatus for rapidly inspecting silicon wafers for the purpose of detecting the presence of photoresist on the wafers and whether the photoresist has been appropriately exposed and patterned.

BACKGROUND OF THE INVENTION

In the processing of semiconductor devices, photoresist materials are used for a variety of applications, including use as etch masks for the fabrication of surface features and implant masks for patterning implants in a semiconductor material. Understandably, significant problems arise if the photoresist material is missing or improperly exposed and/or developed. Without early detection that would permit the use of remedial procedures, semiconductors with improper photoresist coverage must be scrapped at considerable cost.

In response to this problem, the prior art has sought to visually inspect semiconductor wafers to ensure the presence and suitability of their photoresist coverage. For this purpose, the prior art has proposed the use of fluorescence microscopes operating at a wavelength which will cause the photoresist material present on a wafer to fluoresce, though only sufficiently to be detectable with considerable magnification, e.g., about 100× or more. With this method, each wafer is individually placed on a microscope stage, an operator focuses the microscope to obtain a clear image of the wafer, and then illumination radiation is projected along the optical axis of the microscope and focused on the surface of the wafer. The operator must then scan the surface of the wafer to visually determine the presence of the photoresist and evaluate its coverage and patterning.

A single silicon wafer is likely to go through numerous masking levels, an error at any one of which can result in wafer scrap. Because deficient photoresist coverage, exposure and development occur generally randomly at low levels, a 100% inspection rate is often necessary to achieve any significant reduction in wafer scrap. Unfortunately, doing so using the above-noted prior art methods entails significant additional labor and slows processing considerably. Therefore, it would be desirable if an inspection method were available that was capable of accurately and reliably detecting the presence and patterning of a photoresist material on the surface of a substrate, though at a rate vastly higher than that possible with prior art techniques.

SUMMARY OF THE INVENTION

It is an object of this invention to provide a method for detecting the presence, coverage and patterning of a photoresist material on a substrate, such as a silicon wafer being processed to produce a semiconductor device.

It is a further object of this invention that such a method enables a high inspection rate, by which one or more substrates can be rapidly scanned in sequence.

It is another object of this invention that such a method entails the use of an apparatus configured to enable rapid inspection of silicon wafers in a semiconductor processing environment.

In accordance with a preferred embodiment of this invention, these and other objects and advantages are accomplished as follows.

According to the present invention, there is provided a method for inspecting a substrate having a surface on which a photoresist material has been deposited, and preferably patterned. The method achieves a rapid rate of inspection by projecting an illumination beam onto the substrate so as to be incident on at least a portion of the substrate, with the illumination beam being of an appropriate wavelength and of sufficient intensity to cause the photoresist material on the substrate to fluoresce with an intensity that can be detected visually without magnification. Accordingly, the fluorescence of the photoresist material need not be detected with high power magnification equipment, as required by the prior art, and therefore substrates can be scanned through the illumination beam at a relatively high rate. Inspection can be performed manually or automated through optical equipment that can detect flaws in the photoresist based on knowledge of the patterned image desired for the photoresist.

The method of this invention is made possible by an inspection apparatus that preferably includes a device for transporting substrates through the illumination beam, with each substrate being properly aligned with the illumination beam and spaced apart and substantially parallel relative to adjacent substrates. A preferred transport device precisely orients multiple substrates relative to the illumination beam such that portions of the planar surfaces near edges of the substrates are sequentially irradiated by the beam without requiring that the substrates be individually manipulated. Consequently, only a portion of the substrate surface near an illuminated edge is inspected, though sufficient surface area is examined to verify the adequacy of the previous application, exposure and development steps performed on the photoresist material.

According to this invention, the illumination beam is generated and projected onto the substrates by equipment configured to produce a beam having a wavelength and sufficient intensity to cause the photoresist material to fluoresce with an intensity that can be visually detected without magnification, though low power magnification (e.g., 20× or less) may be used if so desired. According to this invention, the illumination beam is produced to have a wavelength that excites the resist fluorescence, typically about 450 to about 500 nanometers (nm), and at an intensity level of at least 50 milliwatts (mW) per square centimeter. In addition, the beam preferably must have a sufficiently homogeneous intensity distribution to be free from spatial intensity variations that would interfere with the optical inspection process. Devices capable of producing a suitable illumination beam include appropriately configured lasers, light-emitting diodes (LEDs), filtered high-intensity arc lamps, and high-intensity black lights.

The apparatus of this invention may include an automated device for detecting the fluorescence of the photoresist material, such as an optical sensing system capable of detecting variances in the intensity of the fluorescence emitted by the photoresist material. Most preferably, a fluorescence filter is employed to block the illumination beam from the device used to detect the fluorescence of the photoresist material.

According to this invention, the apparatus has been found to enable multiple silicon wafers to be rapidly inspected to ensure adequate coverage, exposure and development of photoresist during processing of the wafers. Comparative testing has shown that the inspection rate for this invention is nearly twenty times higher than that typical for prior art inspection methods. This capability is attributed to the manner in which the wafers are transported through the illumination beam, the characteristics of the beam, and the inspection techniques made possible by the type of beam used.

Other objects and advantages of this invention will be better appreciated from the following detailed description.

BRIEF DESCRIPTION OF THE DRAWINGS

The present invention will now be described, by way of example, with reference to the accompanying drawings, in which an inspection apparatus in accordance with this invention is shown schematically in cross section.

DETAILED DESCRIPTION OF THE INVENTION

Illustrated in FIG. 1 is an inspection apparatus 10 that is capable of rapidly inspecting and evaluating the presence and patterning of a photoresist material on substrates in accordance with this invention. While the invention will be discussed in reference to inspecting silicon wafers 12 and the processing of semiconductor devices, those skilled in the art will appreciate that the substrates could be formed of other materials and for other purposes.

As is schematically represented in FIG. 1, the apparatus 10 of this invention operates with an illumination beam 14 incident on planar surfaces near the edges of one or more wafers 12 on which a photoresist material has been applied. The beam 14 is conditioned to cause the photoresist material to fluoresce, producing a fluorescence emission 16 that is detected by sensing equipment 20. A light source 18 and a delivery fiber 24 are schematically shown as generating and delivering the illumination beam 14 to the interior of an enclosure 32 in which the wafers 12 are enclosed for the inspection process. The enclosure 32 is preferably capable of shielding its interior from light from the surrounding environment. In addition, the enclosure 32 preferably has a black diffuse interior surface that will not fluoresce or produce an unacceptable amount of stray light. The wafers 12 are shown as being transported beneath the illumination beam 14 in a cassette 26 placed on a carrier 28 supported by a sliding tray 30, all of which are accommodated within the enclosure 32. An access door 34 to the enclosure 32 permits the tray 30 and its cargo to be inserted and removed as necessary, and preferably prevents operation of the light source 18 while the door 34 is open.

A notable aspect of this invention is that the wafers 12 are oriented by the cassette 26 to be inclined relative to the illumination beam 14, and positioned relative to each other to expose to the illumination beam 14 a limited surface region near an edge of each wafer 12. The cassette 26 preferably aligns the wafers 12 to be spaced apart about five to about ten millimeters from each other and substantially parallel to each other, with each wafer 12 projecting about ten or more millimeters beyond the edge of the preceding wafer 12, such that the wafers 12 are not required to be individually manipulated for inspection. The beam 14 illuminates the surfaces of the wafers 12, producing the fluorescence emission 16 that can be detected by the sensing equipment 20. The tray 30 enables the carrier 28 to traverse the interior of the enclosure 32 in a controlled manner, so that the wafers 12 are sequentially illuminated by the beam 14 when the tray 30 is moved in a leftward or rightward direction as illustrated in the Figure. The carrier 28 preferably maintains the wafers 12 a consistent distance from the sensing equipment 20 so that the equipment 20 need not be continuously refocused during inspection. It is desirable though not necessary for the tray 30 to also move in a transverse direction in order to allow the beam 14 to scan along the edge of an individual wafer 12.

The incident direction of the illumination beam 14 and the angle of the target line of the sensing equipment 20 are critical to implementing this invention. Specifically, the relative orientations of the illumination beam 14, wafers 12 and sensing equipment 20 are selected to avoid direct specular reflection of the illumination beam 14 into the sensing equipment 20, and to avoid reflected light into the sensing equipment 20 from the backside of wafers 12 adjacent to those being inspected. As is shown by example in the Figure, these undesired reflections can be avoided by projecting the illumination beam 14 at an angle of about 45 degrees to the surfaces of the wafers 12, while the target line of the sensing equipment 20 is preferably approximately perpendicular to the surfaces of the wafers 12 so as to ensure that the entire wafer surface within the field of view can be brought into sharp focus with the sensing equipment 20. Foreseeably, other orientations are possible and within the scope of this invention.

According to the above, only a portion of each wafer 12 is irradiated by the beam 14 at any given time, though in practice a sufficient surface area is examined by the method of this invention to provide a reliable evaluation of the photoresist coverage. For this purpose, the beam 14 preferably produces an illumination site having a minimum dimension of at least about five millimeters, preferably a diameter of about one to three centimeters, at the surface of each wafer 12, though it is foreseeable that larger or smaller areas could be illuminated. Importantly, to enable reliable detection of photoresist on the surfaces of the wafers 12 in accordance with the invention, the illumination of the wafers 12 by the beam 14 is preferably clean and uniform. For this reason, the beam 14 is preferably both homogeneous and of high intensity. Suitable high-intensity devices for the light source 18 include lasers, LEDs, filtered high-intensity arc lamps, and high-intensity black lights that are capable of generating an illumination beam 14 having a wavelength and sufficient intensity to cause the photoresist material on the wafers 12 to fluoresce with an intensity that can be visually detected without magnification, though low power magnification (e.g., 20× or less) may be used if so desired. Preferred high-intensity light sources 18 include filtered arc lamps and HeCd and Ar-ion lasers that produce an illumination beam 14 having an intensity level of about 50 mW or more per square centimeter and a wavelength that excites the resist fluorescence, typically about 450 to about 500 nanometers (nm), which cause typical photoresist materials to fluoresce in the red-orange spectral region with an intensity that is sufficient to be visible with the unaided eye. Accordingly, the prior art requirement for a high power microscope is eliminated by this invention.

Because coherent light sources, such as lasers, are subject to diffraction effects, they will tend to produce bright and dark areas in the illumination spot on the wafers 12. Such an occurrence would interfere with the inspection process by making it difficult to distinguish small features in a patterned photoresist. Accordingly, and as shown in the Figure, the apparatus 10 includes an optical fiber 24 to homogenize the intensity distribution of a coherent light source if employed by the method of this invention. Multi-mode optical fibers of types known in the art are suitable for this purpose, including solid core fiber. According to the invention, a liquid-filled light guide of a type known in the art is preferred as not only providing for a homogeneous intensity distribution for the illumination beam 14, but also for being particularly efficient and therefore having minimal effect on the intensity of the light beam emitted by the light source 18. Alternatively, other devices could be used to eliminate the undesirable diffraction effect, such as spatial filters or a series of mirrors, though optical fibers are preferred for their simplicity (i.e., they are not subject to misalignment as would mirrors), convenience, and the ability to homogenize the beam 14 in such a way as to produce a highly uniform illumination intensity.

Once a fluorescence emission 16 of sufficient intensity is produced in accordance with the above, detection of the photoresist material on the wafers 12 becomes a matter of visually confirming the presence of the emission 16 and any discontinuities in the image produced by the emission 16. It will typically be expedient to use a fluorescence filter 22 in order to block any reflection of the illumination beam 14 toward the sensing equipment 20, though other methods could be used to block reflection of the beam 14 in a manner understood by those skilled in the art. The fluorescence emission 16 produced by commercially-available photoresist materials has been found to cover a broad range of wavelengths in the red and near-infrared region (approximately 600 to about 800 nm), necessitating that the filter 22 permit passage of at least a portion of this spectral region for reception by the sensing equipment 20. Various filters having this capability are commercially available and known to those skilled in the art.

Visual examination of the wafers 12 can be performed manually, with the sensing equipment 20 being no more than an eyepiece through which an operator views the wafers 12 through the filter 22. In a preferred embodiment, the sensing equipment 20 includes a video camera with or without recording capability, enabling remote inspection of the wafers 12. Notably, the method of this invention is capable of being highly automated by configuring the sensing equipment 20 to include imaging equipment to detect the fluorescence emission 16 of the photoresist material and develop a sensed image, which is then compared with a stored image to produce an output indicative of any sensed difference between the sensed and stored images. For example, the sensing equipment 20 could comprise an optical sensor connected to a signal processor in which is stored an image of an acceptable photoresist pattern present on the wafers 12. An operator could then enter the identification of the wafers 12, e.g., by bar code, causing the computer to correctly identify the stored photoresist pattern image for the wafers 12. The sensing equipment 20 could then be configured to allow the operator to visually compare the stored image with that detected from the wafers 12, or could automatically compare the images and notify the operator which if any of the wafers 12 has an improperly patterned photoresist.

According to this invention, the apparatus 10 shown in the Figure has been found to enable rapid inspection of silicon wafers 12 at a rate of nearly twenty times higher than that typical for prior art inspection methods. Therefore, those skilled in the art will appreciate that a significant advantage of the apparatus 10 and method of this invention is the capability to enable 100% inspection of wafers during processing without negatively affecting the overall processing costs and throughput for the semiconductor devices being fabricated. This advantage is directly attributable to the ability of the apparatus 10 to rapidly scan a number of wafers 12 with an illumination beam 14 whose intensity and homogeneity enable visual inspection of photoresist without use of magnification.

The apparatus 10 can also be adapted to inspect wafers for pattern alignment between a top photoresist pattern and an underlying pattern by this invention's technique of inducing the photoresist of the top pattern to fluoresce. Some magnification is preferable for achieving this purpose, the level of which depending on the degree of alignment accuracy desired. One method for achieving this alignment inspection is to employ a dual-mode filter 22. In one mode, the filter blocks the illumination beam 14 so as to allow for inspection of the fluorescing pattern only. In the second mode, the filter passes reflections of the illumination beam 14, or some fraction thereof, allowing for inspection of the underlying non-fluorescing pattern. By alternating between the two modes at an appropriate rate, a judgement can be made regarding the alignment accuracy of the fluorescing pattern to the underlying pattern, as would be understood by those skilled in the art.

Alternatively, a similar effect can be achieved by utilizing a secondary illumination source of an appropriate wavelength so that it passes, fully or partially through the blocking filter. Preferably this illumination source is coaxial with the target line of the sensing equipment 20, particularly for substrates containing a high specular reflectance. With the secondary source at an appropriate intensity and wavelength, both patterns may be viewed. Preferably, alternating between the light source 18 and the secondary source at an appropriate rate enables a comparison of position of both patterns, thereby permitting an operator to judge the alignment accuracy between the underlying pattern and the fluorescing pattern. This second technique using coaxial illumination is generally preferable to the dual-mode filter technique for surfaces with a high specular reflectance and small vertical geometries.

While the invention has been described in terms of a preferred embodiment, it is apparent that other forms could be adopted by one skilled in the art. For example, the apparatus of this invention could also be used to inspect the presence and patterning of implants, organic-base spin-on glass and polyimides on a substrate. Accordingly, the scope of the invention is to be limited only by the following claims.

What is claimed is:

1. A method comprising the steps of:
   providing a plurality of substrates, each substrate having a surface on which a photoresist material has been deposited;
   positioning the substrates so as to be spaced apart and substantially parallel to each other;
   sequentially projecting an illumination beam onto each of the substrates so as to be incident on at least a portion of the photoresist material thereon, the illumination beam causing the photoresist material to fluoresce with an intensity sufficient to be visible without magnification; and
   detecting the fluorescence of the photoresist material while avoiding direct specular reflection of the illumination beam.

2. A method as recited in claim 1, wherein the illumination beam is projected at an acute angle to the surface of each substrate, and wherein the fluorescence of the photoresist material is detected along a target line that is approximately perpendicular to the surface of each substrate.

3. A method as recited in claim 1, wherein the illumination beam is generated by a device chosen from the group consisting of lasers, LEDs, filtered high-intensity arc lamps, and high-intensity black lights.

4. A method as recited in claim 1, wherein the illumination beam has a homogeneous intensity distribution on the surface of an individual substrate while the illumination beam is projected at the individual substrate during the projecting step.

5. A method as recited in claim 1, wherein the illumination beam is incident on a portion of a planar surface near an edge of an individual substrate while the illumination beam is projected at the individual substrate during the projecting step.

6. A method as recited in claim 1, wherein the fluorescence of the photoresist material is detected along a target line that avoids direct specular reflection of the illumination beam toward means used to detect the fluorescence of the photoresist material.

7. A method as recited in claim 1, wherein the fluorescence of the photoresist material is detected through a fluorescence filter that substantially blocks the illumination beam from means used to detect the fluorescence of the photoresist material.

8. A method as recited in claim 1, further comprising the step of transporting the substrates through the illumination beam on a carrier, the carrier aligning the substrates to be spaced apart, substantially parallel to each other, and inclined to the illumination beam.

9. A method as recited in claim 1, wherein the detecting step entails detecting the fluorescence of the photoresist material so as to develop a sensed image, comparing the sensed image with a stored image, and outputting a signal if a difference is detected between the sensed and stored images.

10. A method as recited in claim 1, wherein the detecting step entails inspecting pattern alignment between a first photoresist pattern and an underlying photoresist pattern on each of the substrates.

11. A method comprising the steps of:
providing a plurality of silicon wafers, each silicon wafer having a planar surface on which a photoresist material has been deposited and patterned;
positioning the silicon wafers on a carrier that aligns the silicon wafers to be spaced apart and substantially parallel to each other;
transporting the carrier through a homogeneous illumination beam such that the illumination beam is incident on a portion of the planar surface near an edge of each silicon wafer as each silicon wafer is sequentially illuminated by the illumination beam, the illumination beam causing the photoresist material to fluoresce with an intensity sufficient to be visible without magnification; and
detecting the fluorescence of the photoresist material through a fluorescence filter that substantially blocks the illumination beam from means used to detect the fluorescence of the photoresist material.

12. A method as recited in claim 11, wherein the illumination beam is characterized by a wavelength of about 450 nm to about 500 nm and an intensity level of at least 50 mW per square centimeter.

13. A method as recited in claim 11, wherein the illumination beam is generated by a device chosen from the group consisting of lasers and filtered high-intensity arc lamps.

14. A method as recited in claim 11, wherein the illumination beam is delivered to the silicon wafers through a liquid-filled light guide so as to produce a homogeneous intensity distribution on the surfaces of the silicon wafers.

15. A method as recited in claim 11, wherein the fluorescence of the photoresist material is detected along a target line that avoids direct specular reflection of the illumination beam toward the means used to detect the fluorescence of the photoresist material, the illumination beam being projected at an acute angle to the planar surface of each silicon wafer, and the target line along which the fluorescence of the photoresist material is detected is approximately perpendicular to the planar surface of each silicon wafer.

16. A method as recited in claim 11, wherein the detecting step entails detecting the fluorescence of the photoresist material so as to develop a sensed image, comparing the sensed image with a stored image, and outputting a signal if a difference is detected between the sensed and stored images.

17. An inspection apparatus for detecting the presence of patterned photoresist material on a surface of a substrate, the inspection apparatus comprising:
means for transporting a plurality of substrates through the illumination beam, the transporting means aligning the substrates to be spaced apart and substantially parallel to each other;
means for generating and sequentially projecting an illumination beam onto the substrates so as to be incident on at least a portion of a photoresist material on a planar surface of an individual substrate, the illumination beam produced having a wavelength and being of sufficient intensity to cause the photoresist material to fluoresce with an intensity sufficient to be visible without magnification; and
means for detecting the fluorescence of the photoresist material while avoiding direct specular reflection of the illumination beam.

18. An apparatus as recited in claim 17, wherein the illumination beam is characterized by a wavelength of about 450 nm to about 500 nm and an intensity level of at least 50 mW per square centimeter.

19. An apparatus as recited in claim 17, wherein the generating and projecting means is a device chosen from the group consisting of lasers, LEDs, filtered high-intensity arc lamps, and high-intensity black lights.

20. An apparatus as recited in claim 17, further comprising means for causing the illumination beam to have a homogeneous intensity distribution.

21. An apparatus as recited in claim 17, wherein the generating and projecting means and the detecting means cooperate to avoid direct specular reflection of the illumination beam toward the detecting means by the generating and projecting means projecting the illumination beam at an acute angle to the planar surface of each substrate and the detecting means detecting the fluorescence of the photoresist material along a target line that is approximately perpendicular to the planar surface of each substrate.

22. An apparatus as recited in claim 17, further comprising means for substantially blocking the illumination beam from the detecting means.

23. An apparatus as recited in claim 17, wherein the detecting means comprises means for detecting the fluorescence of the photoresist material so as to develop a sensed image, means for comparing the sensed image with a stored image, and means for outputting a signal if a difference is detected between the sensed and stored images.

* * * * *